United States Patent [19]

Batchelor et al.

[11] Patent Number: 4,563,468

[45] Date of Patent: Jan. 7, 1986

[54] CHEMOTHERAPEUTIC AGENTS

[75] Inventors: John F. Batchelor; Harold F. Hodson, both of Beckenham; John W. T. Selway, Cranbrook, all of England

[73] Assignee: Burroughs Wellcome Co., Research Triangle Park, N.C.

[21] Appl. No.: 177,126

[22] Filed: Aug. 11, 1980

[30] Foreign Application Priority Data

Sep. 13, 1979 [GB] United Kingdom ................ 7931840

[51] Int. Cl.$^4$ .................... A61K 31/44; C07D 405/04
[52] U.S. Cl. ...................................... 514/337; 546/269
[58] Field of Search ........................ 546/269; 424/263; 514/337

[56] References Cited

U.S. PATENT DOCUMENTS 4,237,162  12/1980  Kabbe et al. ...................... 546/269

FOREIGN PATENT DOCUMENTS 2148363  3/1973  France .
70267    1/1952  Netherlands .

OTHER PUBLICATIONS

Tyrrell et al., *J. Antimicrob. Chem.*, 9/5, pp. 340–341 (1982).

*Primary Examiner*—John M. Ford
*Attorney, Agent, or Firm*—Donald Brown

[57] ABSTRACT

2-Pyridyl chroman and derivatives thereof have been discovered to have potent anti-viral activities, i.e. particular against rhinovirus. Novel compounds and their pharmaceutically acceptable salts, pharmaceutical formulations containing the compounds of this invention and the treatment of viral infections with these formulations are all disclosed. 2-(3-Pyridyl)chroman and 6-chloro-2-(3-pyridyl)chroman are examples of especially active compounds of this invention.

25 Claims, No Drawings

CHEMOTHERAPEUTIC AGENTS

The present invention relates to 2-pyridyl chroman and derivatives thereof which are useful as medicaments. In particular such compounds are antiviral agents and are especially suitable for the prevention and treatment of rhinoviral infections. The invention also relates to processes for the production of these compounds, to pharmaceutical formulations containing them and to methods of treatment employing them.

In the majority of instances, the disease known as the "common cold" is caused by rhinoviral infections, although "colds" may also be caused by infection of the upper respiratory tract by e.g. corona- and enteroviruses, and allergic reactions may be mistaken for colds. Mankind throughout the world is prone to rhinoviral infections, which are a major cause of absence from work through illness. The prevention and treatment of such diseases is thus of great economic importance.

Once infected by a rhinovirus, an individual retains immunity to that serotype, which may be enhanced by continual reinfection if the serotype is prevalent in the community. There is, however, no cross-immunity between serotypes and thus a cold is usually experienced by an individual whenever a new serotype of rhinovirus is encountered, on average about twice or three times a year.

Immunisation against rhinovirus is not practicable because there are about 120 known serotypes of rhinovirus and a vaccine against all these would overload the vaccinee's immune system.

It would therefore appear that chemotherapy is the only suitable method for preventing or treating rhinoviral infections. Much research effort has been expended in recent years but no effective chemotherapeutic agent has yet emerged.

It has been found 2-pyridylchroman and derivatives thereof are active against rhinovirus.

According to the present invention there is therefore provided a compound of formula (I)

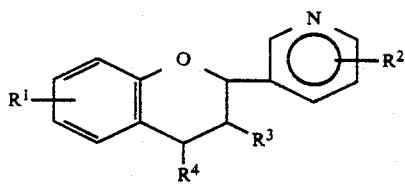

or tautomers thereof, wherein $R^1$ and $R^2$ each represent four substituents independently selected from hydrogen and halogen atoms, (lower)alkyl, hydroxy(lower)alkyl, carboxy(lower)alkyl, (lower)alkoxyl, amino, (lower)alkylamino, di(lower)alkylamino, acylamino, nitro, cyano, trifluoromethyl, carboxyl, hydroxyl and methylenedioxy groups and $R^3$ and $R^4$ are the same or different and each is selected from hydrogen atoms and (lower)alkyl groups, and the N-oxides of such compounds and salts or esters of such compounds, where appropriate.

As used herein the expressions "(lower)alkoxyl" and "(lower)alkyl" and cognate terms, mean straight or branched chain alkyl or alkoxyl groups having from 1 to 4 carbon atoms.

As used herein the term "acylamino" means an amino group substituted with the residue of a carboxylic acid, in particular a (lower)alkyl, aryl(lower)alkyl or aryl carboxylic acid.

For the purposes of this description, the numbering system shown below is used to denote the various atoms of the 2-pyridyl chromans of the present invention:

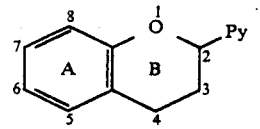

where Py is a pyridyl group and the atoms of the pyridyl group are numbered:

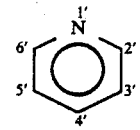

It will be appreciated that the pyridyl group may be linked to the 2-position of the chroman ring system, by either the 3' or 5' atom.

Whenever the pyridyl group has hydroxy substituents in the 2' or 4' or 6' positions, tautomeric forms, such as the following, will exist

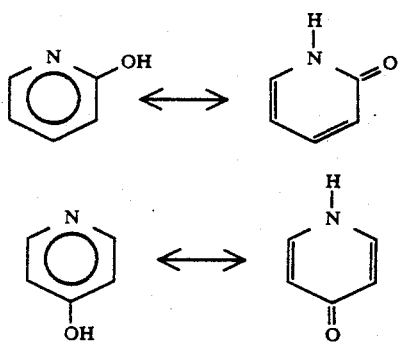

Whenever a compound of formula (I) bears a hydroxyl, amino or carboxyl group, salts and esters may be formed. Acid addition salts may also be formed with the nitrogen atom of the pyridyl group. It is preferred that these salts and esters be pharmaceutically acceptable. A discussion of the properties and desirability of various salts is given in "Pharmaceutical Salts" by S. M. Berge et al., J.Pharm. Sci g 66,I(1977).

It will be noticed that compounds of formula (I) may exist in various stereoisomeric forms depending upon the configuration of the substituents on the carbon atoms designated 3 and/or 4 in formula (I) in relation to the pyridyl group on carbon atom 2. Whilst the present invention encompasses all the possible enantiomers, diastereomers and geometrical isomers of compounds of formula (I) certain stereoisomers are preferred because they have enhanced antiviral activity. In particular, when $R^3$ is an alkyl group it is preferred that this group be in the trans-configuration with respect to the pyridyl group.

It is preferred that one, or more preferably both of $R^3$ and $R^4$ are hydrogen atoms.

Wherever $R^3$ or $R^4$ is a (lower) alkyl group it is preferred that the alkyl group has 1 to 3 carbon atoms, most preferably it is a methyl or ethyl group, especially a methyl group.

Whilst $R^1$ and $R^2$ may each represent up to four atoms or groups other than hydrogen atoms, it is preferred that at least two of the substituents represented by $R^1$ and/or at least two of the substituents represented by $R^2$, are hydrogen atoms.

Particularly preferred substituents are hydrogen and halogen atoms and amino, hydroxyl, methyl, ethyl, methoxy, ethoxy, hydroxymethyl, cyano and trifluoromethyl groups.

It is preferred that substituents other than hydrogen atoms represented by $R^1$ are located at the 6, and/or 7 of a compound of formula (I), most preferably the 6 position.

More preferred compounds of formula (I) are those wherein $R'$ represents three hydrogen atoms at the 5, 7 and 8 positions and a substituent selected from the abovementioned class at the 6 position.

Compounds of formula (I) representing a conjunction of two or more of the preferences stated hereinbefore are most particularly preferred embodiments of the present invention.

The most preferred compounds of formula (I) are the following, namely:

2-(3-pyridyl)chroman
6-chloro-2-(3-pyridyl)chroman
and the N-oxides thereof.

In a particular aspect of the present invention there is provided a compound of formula (I) as a medicament, such a compound being particularly suitable for treating or preventing viral, especially rhinoviral, diseases.

Several processes are available for the production of compounds of formula (I), these being analogous to the synthetic methods known and used in the preparation of flavanoids (flavanoids being 2-phenylchroman derivatives) as illustrated in the literature cited hereunder.

The three synthetic routes to flavanoids are (a) the reduction of a flavylium salt, or of substituents on, or double bonds in the "B" ring or (b) the reduction and cyclisation of 2-hydroxychalcones or (c) the condensation of unstable precursors, or the quinone methide obtained therefrom, with an aromatic olefin derivative. These methods, which are illustrated in the literature cited hereunder, may also be applied to the production of 2-pyridylchromans of formula (I)

Accordingly, 2-pyridylchromans may be produced, (a), by reduction of 2-pyridylbenzopyrylium salts, -2-H-benzopyrans, -chromanones or -chromones:

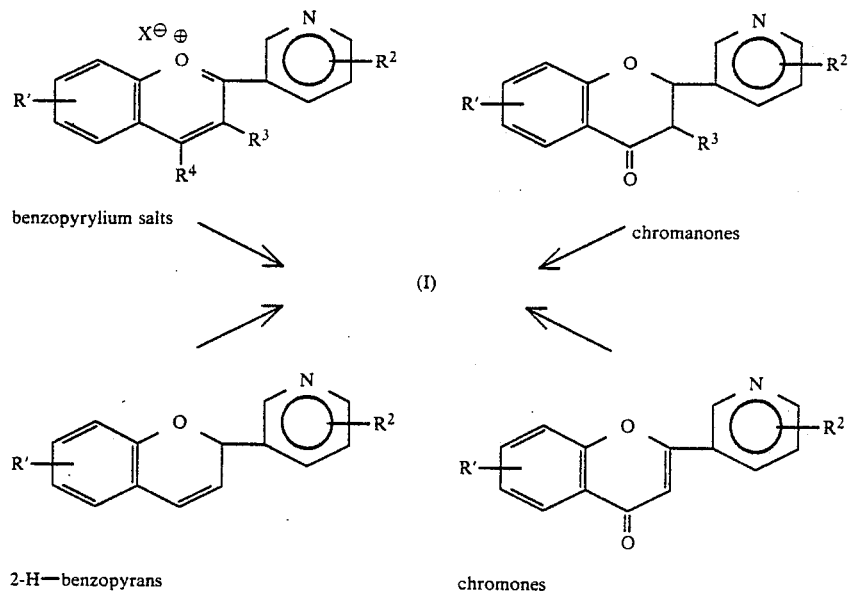

benzopyrylium salts chromanones (I)

2-H—benzopyrans chromones

Such reduction processes may be effected by chemical or catalytic techniques. Exocyclic double bonds and other reducable moieties in precursors for $R^3$ and/or $R^4$ such as alkenyl and alkylidene groups may also be reduced to afford compounds of formula (I), of chromanones.

The clemmensen reduction and catalytic hydrogenation of 2-H-benzopyrans are particularly convenient techniques for producing 2-pyridylchromans. Chromanones may also be converted to chromans by forming the dithioketals which are then converted to the required compound using Raney nickel.

Alternatively, the 2-pyridylchromans of formula (I) may be obtained by, (b), reduction and cyclisation of 1-(2-hydroxyphenyl)-3-pyridyl-propen-1-ones (i.e. "2-hydroxyazachalcones"). Thus, treatment with reducing agents such as sodium borohydride affords the propan-1-ol which is then cyclised under acid conditions, to the 2-pyridylchroman. Catalytic reduction of the 2-hydroxyazachalcones gives the corresponding dihydroazachalcone. Combined reduction and cyclisation of 2-hydroxyazachalcones may be effected using lithium aluminium hydride and aluminium chloride.

A third technique for producing 2-pyridylchromans is, (c), the condensation of a thermally unstable phenol derivative or the quinone methide obtained therefrom with a vinyl pyridine derivative, the reaction being effected thermally or by acid catalysis in certain cases, using proton acids or Friedel Crafts type catalysts. Thus, for example, a 2-hydroxymethylphenol condenses thermally with vinylpyridine to afford the 2-pyridylchroman.

Once the 2-pyridylchroman ring system has been produced, further compounds of formula (I) may be formed by addition, replacement, elimination or modification of the substituents on the aromatic rings although it is usually more convenient to use starting materials which already bear the requisite substituents.

When a substituent, such as a hydroxyl or amino group could interfere with the desired synthetic process it may, of course, be blocked by conventional means such as acylation and later deblocked to afford the desired compound of formula (I)

Chromanones, chromones, 2-H-benzopyrans and benzopyryllium salts used as starting materials for the production of 2-pyridylchromans may themselves be prepared by known methods. Chroman-4-ones suitable for reduction to 2-pyridylchromans according to method (a) above are particularly well known in the literature.

In particular, 2-hydroxyazachalcones may be cyclised to benzopyrylium salts, whilst 2'-hydroxyazachalcones can be reduced and then cyclised to the 2-$\underline{H}$-benzopyrans or may be cyclised directly, affording chromanones. Azachalcones are produced from appropriately substituted o-hydroxy acetophenone and pyridine carboxaldehyde derivatives or from appropriately substituted salicylaldehydes and acetyl pyridine derivatives by Knoevenagel condensation. 2-Pyridylchroman N-oxides of formula (I) are produced by oxidation of the corresponding 2-pyridylchroman using peroxide reagents such as hydrogen peroxide, peracetic acid or m-chloroperbenzoic acid, or from the N-oxides of appropriate precursors of 2-pyridylchromans by the processes described above. The N-oxides may be reduced to 2-pyridylchromans using agents such as a phosphorus trihalide, especially the tribromide, and trimethylphosphite.

When appropriate, when preparing compounds of formula (I) which may exist in cis and trans forms, particular attention should be paid to the stereochemistry of the reactions employed, since some are more suitable for obtaining cis isomers and others are better adapted to the production of the trans isomers. Obviously not all the reactions are stereospecific or stereoselective and in these cases, separation steps such as chromatography may be required in order to obtain a particular geometric isomer in a pure form.

By selecting a particular enantiomer of a starting material and using an asymmetric synthesis, an optically pure enantiomer of a compound of formula (I) may be obtained, (e.g. Corey & Mitra, *J.Am.Chem.Soc.*, 84, 2938, (1962)) Alternatively, where suitable, optical resolution of a compound of formula (I) may be possible by the use of asymmetric reagents or chromatographic media.

Literature cited in relation to processes for producing 2-arylchromans:

E. L. Martin, *Organic Reactions*, 1,161,(1942)
E. Vedejs, *Organic Reactions*,22,412,(1974)
B. L. Verma, et al.,*Indian J.Chem.*,3(12),565, (1965)
M. M. Bokadia and B. L. Verma, *Chem. and Ind.*,235, (1964)
British Patent Specification No.1022745
British Patent Specification No.1087539
U.S. Pat. No. 3,555,047
M. M. Bokadia, et al., *J. Chem Soc.*,1658, (1962)
J. W. Clark-Lewis and R. W. Jemison, *Austral.J.-Chem.*,21,2247,(1968)
M. Suzuki, et al., *Nippon Kagaku Zasshi,*89(9),878, (1968) and ibid,90(4), 397, (1969)
R. Mozingo and H. Adkins, *J.Am. Chem. Soc.*, 60, 669, (1938)
L. Jurd, Tetrahedron, 23, 1057, (1967)
E. J. Keogh, et al., *Chem. and Ind.*, 2100, (1961)
L. Jurd, *Chem. and Ind.*,2175, (1967)
R. R. Schmidt, *Tet.Letters,*60,5279, (1969)
K. Hultzch, *J. Prakt.Chem.,*158,275, (1941)
M. Wakselman and M. Vilkas, *C. R. Hebd.Seances and Acad Sci.,*258, 1526 (1964)
Nielsen, *Organic Reactions,* 16, 44, (9168)
J. Andrieux, et al., *Bull. Soc. Chem. France,* 1967, (1976)
G. Descotes and A. Jullien, *Tet. Letters,* 39, 3395, (1969)
Courvaiser, *Compt. Rendn.*, 251,1641, (1960)
Courvaiser, *Bull. Soc. Chim.France* 528, (1962)
Annigeri and Siddappa: *J.Karnatak Univ.*, 9–10,21, (1964–5);
Annigeri and Siddappa: *J. Karnatak Univ.*, 11, 1, (1966).
Kuhn and Hensel; *Chem. Ber.*, 86, 1333, (1953).
Cheng, Foumari, and Tirouflet, *Bull. Soc. Chim. Fance,* 10,224, (1963)
Sanya and Yeruo; *Takugaku Zasshi,* 88(8)1020,(1968); (C.A.,70, 11526x)
Annigeri and Siddappa; *Indian.J.Chem.*, 2(10), 413, (1964).
Boehme and Koo; *J. Org. Chem.*, 26, 3589, (1961).
Koo; *J. Org. Chem.*, 26,4185, (1961)
Annigeri and Siddappa; *Monatsh. Chem.*, 96(2),625, (1965)

While it is possible for the compounds of formula (I) or, where appropriate, pharmaceutically acceptable salts thereof (hereinafter referred to as the "active compounds") to be administered as the raw chemical it is preferred that the active compound is presented in the form of a pharmaceutical composition.

In a further aspect of the invention there is therefore provided a pharmaceutically formulation comprising the active compound together with a pharmaceutically acceptable carrier therefor. The carrier must be "acceptable" in the sense of being compatible with the other ingredients of the formulation and not deleterious to the recipient thereof. Such carriers are solid, liquid or gaseous materials recommended for the purpose of administering the medicament. The terms "formulation" and "composition" are used herein synonomously.

These pharmaceutical compositions may be administered orally or parenterally (including subcutaneous, intramuscular and intravenous injection) or as a suppository or pessary or may be applied topical or as an ophthalmic solution, or may be inhaled. It is preferred that the compositions are administered orally or inhaled.

For oral administration the pharmaceutical compositions may be presented as a draught in water or in a syrup, in capsules, cachets, boluses or tablets, as an aqueous or oleaginous solution or suspension, or in suspension in a syrup, such suspensions optionally including suspending agents, or as an oil-in-water or water-in-oil emulsion. Where desirable or necessary, flavouring, sweetening, preserving thickening or emulsifying agents may be included in the formulation.

Tablets may contain the active compound as a powder or granules optionally mixed with binders, lubricants, inert diluents or surface-active or dispersing agents and may be formed by compression or by moulding in inert liquid diluent. Such tablets may be optionally scored and/or coated.

Capsules and cachets may contain the active compound alone or in admixture with one or more accesary ingredients. Capsules may also contain the active compound in aqueous or oleaginous solution, suspension or emulsion, optionally in association with accessory ingredients.

For administration as a suppository or pessary the active compound may be presented in admixture with a suitable carrier such as cocoa butter and other material commonly used in the art, the formulation conveniently being shaped by moulding.

For administration in discrete dosage forms such as the tablets, capsules, suppositories and pessaries described above, the active compound is preferably presented at 0.1 mg to 100 mg most preferably 1 mg to 10 mg per tablet, capsule, suppository or pessary.

For parenteral administration the active compound may be presented in sterile solutions or suspensions in aqueous or oleaginous vehicles, which may also contain preservatives and materials for rendering the solution or suspension isotonic with the blood of the intended recipient. Such formulations may conveniently be presented in unit dose or multi-dose sealed containers.

For topical administration the composition may be presented in ointments, creams, lotions, pastes, jellies, sprays, aerosols and bath oils. Ointments and creams may have oleaginous, absorption and colloidal clays, bases and may include thickening agents such as gum tragacanth or sodium alginate and other pharmaceutically acceptable accessory ingredients such as humectants, preservatives, buffers and antioxidants which are useful in such formulations.

For administration as eye drops, the active compound is presented in sterile water with excipients such as antimicrobial agents and antioxidants as a relatively dilute solution.

For administration orally in liquid form or parenterally or as eye or nose drops the active compound is preferably presented in solution or suspension or emulsion at a concentration of from 0.1 to 10%, more preferably 0.2 to 5% w/v in unit or multi-dose forms. When presented in unit dose form it is preferred that each dose unit contains 0.1 mg to 100 mg, preferably 1 mg to 10 mg of active compound.

For inhalation the active compound may be presented in association with volatile excipients, as a cream, lotion, paste or ointment or as a finely divided dry powder or in solution for inhalation through a nasal spray, atomiser or insufflator.

All the above formulations are produced by processes which comprise bringing into association the active compound and one or more carriers.

According to the present invention there is therefore provided a process for producing a pharmaceutical formulation of a compound of formula (I) comprising bringing into association a compound of formula (I) and a pharmaceutically acceptable carrier therefore.

Compounds of formula (I) may be administered to human being and to other animals to treat or prevent viral diseases, especially rhinoviral infections. The dosage administered obviously depends on the activity of the active compound and also on the speed with which it is absorbed into the body and on other well-known pharmacological considerations, however it is recommended that the active compound is administered at from 2 μg to 10 mg/kg of animal body weight per day, preferably from 25 μg to 1 mg/kg/day and most preferably about 0.1 to 0.3 mg/kg/day. The active compound may be administered once or several times daily.

In a further aspect of the present invention there is therefore provided a method for treating rhinoviral infections comprising the administration in an effective dosage, of a compound of formula (I) or a pharmaceutical formulation thereof to a human being or other animal.

In a yet further aspect of the present invention there is provided a method for preventing rhinoviral infections comprising the administration in an effective dosage, of a compound of formula (I) of a pharmaceutical formulation thereof, to an apparently healthy human being or other animal.

As used herein the term "effective dosage" means that quantity of a compound of formula (I) which is sufficient to cure or prevent a rhinoviral infection.

The invention will now be illustrated with reference to the following Examples, which are not intended to limit the invention in any way. Temperatures are given hereunder in degrees Celsius. Pressures are given hereunder in millimeters of mercury ("mmHg"). 1 mm Hg = 133.322 Pa.

EXAMPLE 1

Preparation of 2-(3-pyridyl)chroman (i) o-Hydroxyacetophenone (20.4 g) and pyridine-3-aldehyde (16.05 g) were dissolved in ethanol (200 ml) and a solution of potassium hydroxide (30.0 g) in water (10 ml.) was added. The solution was allowed to stand at room temperature for 5 hr., then was acidified with acetic acid (50 ml.) in water (200 ml.) The yellow precipitated product was filtered off, washed with water, and recrystallised from ethanol to give 1-(2-hydroxyphenyl-3-(3-pyridyl)-2-propan-1-one (11.85 g.), m.pt. 153°–154°.

(ii) 1-(2-Hydroxyphenyl)-3-(3-pyridyl)-2-propan-1-one (11.35 g) was suspended in ethanol (200 ml.), and sodium borohydride (3.50 g) was added in small portion over 5 min. with stirring. The exothemic reaction resulted in a temperature rise to 42° in 10 min. The reaction mixture was stirred for 30 min., the solvent evaporated and the residue diluted with water. The oily insoluble reduction product was extracted into dichloromethane, and the extract dried and evaporated. The residual product was dissolved in acetic acid (50 ml.) and the solution heated at 90° for 2 hr. The acetic acid was evaporated and the residue chromatographed or alkaline alumina, eluting with dichloromethane to yield 2-(3-pyridyl)-2-H-chrom-3-ene, (5.80 g), which was dissolved in acetic acid (100 ml.) and hydrogenated for 18 hrs. at 60° and 13 atm. using 10% w/w palladium on carbon catalyst, The reaction mixture was filtered, evaporated, and the residue chromatographed on alkaline alumina. Elution with toluene gave, on recrystallisation from ethanol, 2-(3-pyridyl)chroman, (4.60 g), m.pt. 59°–60°.

Microanalysis: Theory C: 79.60%; H: 6.20%; N: 6.63%. Found C: 79.52%; H: 6.28%; N: 6.42%.

EXAMPLE 2

Preparation of 2-(3-pyridyl)chroman N-oxide 2-(3-Pyridyl)chroman (1.06 g) was suspended in acetic acid (10 ml.) and hydrogen peroxide solution (30% w/v 0.75 ml.) was added. The mixture was warmed at 70° for 1 hr., then further hydrogen peroxide solution (0.25 ml) was added and the solution kept at 70° for a further 2 hr. The solution was diluted with water and neutralised with solid sodium carbonate. The product was extracted into chloroform and the extract dried and evaporated. Recrystallisation of the residue from carbon tetrachloride gave 2-(3-pyridyl)-chroman N-oxide (0.55 g., m.pt. 119°–121°).

Microanalysis: Theory: C: 73.99%; H: 5.76%; N: 6.16%. Found: C: 73.71%; H: 5.34%; N: 5.92%.

EXAMPLE 3

Preparation of 6-chloro-2-(3-pyridyl)chroman (i) Starting from 5-chloro-2-hydroxyacetophenone and pyridine-3-aldehyde, 1-(5-chloro-2-hydroxyphenyl)-3-(3-pyridyl)-2-propen-1-one (m.pt 145°–146°) was prepared by a method exactly analogous to that used in Example I (i)

(ii) Using the 1-(5-chloro-2-hydroxyphenyl)-3-(3-pyridyl)-2-propen-1-one so prepared, 6-chloro-2-(3-pyridyl)chroman, m.pt. 60°–63° was prepared by a method exactly analogous to that used in Example 1 (ii)

Microanalysis: Theory: C: 68.43%; H: 4.92%; N: 5.70%. Found: C: 68.50%; H: 5.94%; N: 5.57%.

EXAMPLE 4

Assay of activity of compounds of formula (I)

Activity may be detected by the plaque inhibition (PI) test and measured by the plaque reduction (PR) test. Both assays involve the formation of a monolayer cell culture in a petri dish followed by infection with a virus suspension, and then overlaying the culture with nutrient agarose in the form of a gel. This gel ensures that there is no spread of virus throughout the culture and thus areas of localised cell destruction or plaques are formed.

In the plaque inhibition test a filter paper disc which holds 0.01 ml when impregnated with a solution of compound is placed on top of the agarose gel. The compound may then diffuse throughout the gel so that its greatest concentration will be around the disc and its lowest concentration towards the periphery of the petri dish. The efficacy of the compound may be detected by observing the zone of inhibition of plaque formation.

Detectable activity is measured with the plaque reduction assay. A range of concentrations of compound of known molarity are incorporated in the nutrient agarose overlay. Plaque suppression is proportional to compound concentration. Plaque numbers are expressed as percentages of a control, and a dose response curve may be drawn. From this curve 50% of the effective dose (ED$_{50}$) may be estimated.

RESULTS:

| Compound | PR(ED$_{50}$) |
|---|---|
| 2-(3-pyridyl)chroman | 0.39 μM |
| 6-chloro-2-(3-Pyridyl)chroman | 0.042 μM |
| 2-(3-pyridyl)chroman N—oxide | 1.10 μM |

EXAMPLES 5 TO 14

The following compositions were prepared according to the techniques known in the art of pharmacy.

EXAMPLE 5

An inhalant for use in an insufflator was prepared from the following ingredients

| 6-choro-2-(3-pyridyl)-chroman | 0.6 g |
|---|---|
| isopropylmyristate | 10. g |
| Tweed 80 | 0.5 g |
| Span 80 | 0.5 g |

| -continued | |
|---|---|
| methyl-p-hydroxybenzoate | 0.1 g |
| Water to | 100 ml |

EXAMPLE 6

A suspension for use as nose drops was prepared from the following ingredients

| 6-chloro-2-(3-pyridyl)chroman | 0.6 g |
|---|---|
| Keltrol | 0.1 g |
| Sodium Chloride | 0.5 g |
| Sodium lauryl sulphate | 0.1 g |
| Methyl-p-hydroxybenzoate | 0.1 g |
| Water to | 100. ml |

EXAMPLE 7

Capsule 1

| 6-chloro-2-(3-pyridyl)chroman | 6 g |
|---|---|
| Spray-dried lactose | 300 g. |

Gelatin capsules (size 0) were each filled with 500 mg. of the formulation, affording 10 mg. of active ingredient per capsule.

EXAMPLE 8

Capsule 2

| 6-chloro-2-(3-pyridyl)chroman | 6 g |
|---|---|
| Spray-dried lactose | 208 g |
| Maize starch | 20.8 g |
| Polyvinylpyrollidine | 5.2 g |

Gelatin capsules (size 1) were each filled with 400 mg. of the formulation, affording 10 mg. of the active ingredient per capsule.

EXAMPLE 9

Tablet of 6-chloro-2-(3-pyridyl)chroman

A tablet formulation containing a mixture of 6-chloro-2-(3-pyridyl)chroman (10 mg), lactose (90 mg), maize starch (10 mg) and magnesium stearate (1 mg) is prepared by wet granulation.

EXAMPLES 10 and 11

Tablet formulation of the compounds of Example 1 and 2 were prepared by a method exactly analogous to that of Example 9.

EXAMPLE 12

Oil formulation of 6-chloro-2-(3-pyridyl)chroman

| 6-chloro-2-(3-pyridyl)chroman | 1 g |
|---|---|
| olive oil B.P. | 1 g. |

The compound was dissolved in olive oil for use by oral administration.

EXAMPLE 13 AND 14

Oil formulations of the compounds of Example 1 and 2 were prepared by a method exactly analogous to that of Example 12.

EXAMPLE 15

Intranasal Administration-Simulation in vitro

Petri dishes were prepared, as for the plaque inhibition test and the confluent sheet of cells was covered with a layer of agarose gel. The compound, 2-(3-pyridyl)chroman (1 μg) was dissolved in ethanol, and applied to the lids of the petri dishes. When the ethanol had evaporated, leaving the compound spread over the inside of the lids, these were replaced on the petri dishes. Sufficient compound penetrated the agarose layer to cause total inhibition of plaque formulation.

We claim:

1. A compound of formula (I), or N-oxide thereof,

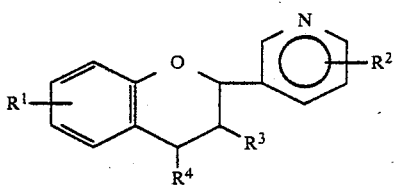

or, tautomers thereof, or where appropriate a salt or ester thereof, wherein $R^1$ and $R^2$ each represent four substituents selected from hydrogen and halogen atoms, (lower) alkyl, hydroxy (lower) alkyl, carboxy (lower) alkyl, (lower) alkoxyl, amino, (lower) alkylamino, di(-lower) alkylamino, (lower)alkanoylamino, nitro, cyano, trifluoromethyl, carboxyl, hydroxyl and methylenedioxy groups and $R^3$ and $R^4$ are the same or different and each is selected from hydrogen atoms and (lower) alkyl groups.

2. A compound according to claim 1 wherein $R^1$ and $R^2$ each represent four substituents selected from hydrogen and halogen atoms and amino, hydroxyl, methyl, ethyl, methoxy, ethoxy, hydroxymethyl, cyano and trifluoromethyl groups.

3. A compound according to claim 1 or claim 2 wherein at least two of the substituents represented by $R^1$ and at least two of the substituents represented by $R^2$ are hydrogen atoms.

4. A compound according to claim 3 wherein $R^1$ represents three hydrogen atoms at the 5, 7 and 8 positions and a substituent selected from hydrogen or halogen atom and amino, hydroxyl, methyl, ethyl, methoxy, ethoxy, hydroxymethyl, cyano and trifluoromethyl group at the 6 position.

5. A compound according to claim 1 wherein both $R^3$ and $R^4$ are hydrogen atoms.

6. A compound according to claim 1 characterised in that $R^3$ and $R^4$ is a methyl or ethyl group.

7. 2-(3-Pyridyl)chroman, 6-chloro-2-(3-pyridyl)chroman and the N oxides thereof.

8. The compound of claim 1 or 2 in which at least two of the substituents represented by $R^1$ and at least two of the substituents represented by $R^2$ are hydrogen atoms.

9. The compound of claim 1 in which $R^3$ or $R^4$ is a methyl or ethyl group.

10. A pharmaceutical composition comprising a compound of formula (I) or the N oxide thereof,

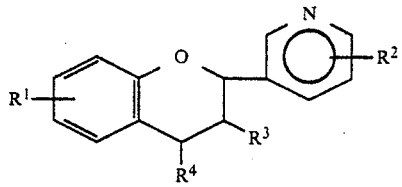

or tautomers thereof, or where appropriate a salt or ester thereof, wherein $R^1$ and $R^2$ each represent four substituents selected from hydrogen and halogen atoms, (lower) alkyl, hydroxy (lower) alkyl, carboxy (lower) alkyl, (lower) alkoxyl, amino, (lower) alkylamino, di(-lower) alkylamino, (lower)alkanoylamino, nitro, cyano, trifluoromethyl, carboxyl, hydroxyl and methylenedioxy groups and $R^3$ and $R^4$ are the same or different and each is selected from hydrogen atoms and (lower) alkyl groups together with a pharmaceutically acceptable carrier therefore.

11. A pharmaceutical composition according to claim 10 characterised in that the compound of formula (I) is 2-(3-pyridyl)chroman or the N-oxide thereof, 6-chloro-2-(3-pyridyl)chroman or the N-oxide thereof.

12. A method of treating rhinoviral infections in a human being or other animal comprising the administration to said human or other animal of an effective, non-toxic antirhinoviral amount of a compound of formula (I) as claimed in claim 1.

13. A method of treating rhinoviral infections in a human being or other animal comprising the administration to said human or other animal of an effective, non-toxic antirhinoviral amount of a compound of formula (I) as claimed in claim 7.

14. A method of treating rhinoviral infections in a human being or other animal comprising the administration to said human or other animal an effective antirhinoviral infection treatment amount of a pharmaceutical composition as claimed in claim 10.

15. A method of treating rhinoviral infections in a human being or other animal comprising the administration to said human or other animal an effective antirhinoviral infection treatment amount of a pharmaceutical composition as claimed in claim 11.

16. A method for preventing rhinoviral infections in an apparently healthy human being or other animal comprising the administration to said human or other animal of an effective non-toxic, antirhinoviral amount of a compound of formula (I) as claimed in claim 1.

17. A method for preventing rhinoviral infections in an apparently healthy human being or other animal comprising the administration to said human or other animal of an effective non-toxic, antirhinoviral amount of a compound of formula (I) as claimed in claim 7.

18. A method for preventing rhinoviral infections in an apparently healthy human being or other animal comprising the administration to said human or other animal an effective antirhinoviral infection treatment amount of a pharmaceutical composition as claimed in claim 10.

19. A method of preventing rhinoviral infections in an apparently healthy human being or other animal comprising the administration to said human or other animal an effective antirhinoviral infection treatment amount of a pharmaceutical composition as claimed in claim 11.

20. The pharmaceutical composition according to claim 10, 11 or 8 in a form for inhalation.

21. The pharmaceutical composition of claim 10, 11 or 8 in a form for oral administration.

22. The composition of claim 10, 11 or 8 in the form of a tablet or capsule.

23. 6-chloro-2-(3-pyridyl)chroman.

24. A pharmaceutical composition comprising the compound 6-chloro-2-(3-pyridyl)chroman together with a pharmaceutically acceptable carrier therefor.

25. A method of treating rhinoviral infections in a human being comprising the administration to the human being of an effective, non-toxic antirhinoviral amount of 6-chloro-2-(3-pyridyl)chroman and a pharmaceutically acceptable carrier therefor.

* * * * *